US00PP30936P2

(12) United States Plant Patent
Stewart et al.

(10) Patent No.: US PP30,936 P2
(45) Date of Patent: Oct. 15, 2019

(54) STRAWBERRY PLANT VARIETY NAMED 'DRISSTRAWSIXTYFOUR'

(50) Latin Name: ***Fragaria* x *ananassa***
Varietal Denomination: DrisStrawSixtyFour

(71) Applicant: Driscoll's, Inc., Watsonville, CA (US)

(72) Inventors: Philip J. Stewart, Watsonville, CA (US); Esther Kibbe, Alden, CA (US); Raymond L. Jacobs, III, Watsonville, CA (US); Mary M. Calkins, Plant City, FL (US)

(73) Assignee: DRISCOLL'S, INC., Watsonville, CA (US)

( * ) Notice: Subject to any disclaimer, the term of this patent is extended or adjusted under 35 U.S.C. 154(b) by 2 days.

(21) Appl. No.: 15/998,031

(22) Filed: Jun. 14, 2018

(51) Int. Cl.
*A01H 5/08* (2018.01)
*A01H 6/74* (2018.01)

(52) U.S. Cl.
USPC ..... Plt./208
CPC ..... *A01H 6/74* (2018.05); *A01H 5/08* (2013.01)

(58) Field of Classification Search
USPC ..... Plt./208, 209
CPC ..... A01H 5/0893
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 López
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.

(Continued)

OTHER PUBLICATIONS

Fear, et al., Unpublished U.S. Appl. No. 15/998,014, filed Jun. 11, 2018, titled "Strawberry Plant Variety Named 'DrisStrawFiftyEight'".
Ferguson et al., Unpublished U.S. Appl. No. 15/731,546, filed Jun. 26, 2017, titled "Strawberry Plant Variety Named 'DrisStrawFiftySix'".
Kibbe et al., Unpublished U.S. Appl. No. 15/731,542, filed Jun. 26, 2017, titled "Strawberry Plant Variety Named 'DrisStrawFiftyTwo'".
Kibbe et al., Unpublished U.S. Appl. No. 15/731,545, filed Jun. 26, 2017, titled "Strawberry Plant Variety Named 'DrisStrawFiftyOne'".

(Continued)

*Primary Examiner* — Kent L Bell
(74) *Attorney, Agent, or Firm* — Morrison & Foerster LLP

(57) ABSTRACT

A new and distinct variety of strawberry plant named 'DrisStrawSixtyFour', particularly characterized by its fruit size and shape, overall productivity and minimal gaps in production, excellent flavor, texture, and juiciness of the fruit, consistency of eating quality throughout season, plant vigor and health, plant architecture, and long and sturdy fruit stems, is disclosed.

4 Drawing Sheets

(56) References Cited

U.S. PATENT DOCUMENTS

| | | | |
|---|---|---|---|
| PP19,767 | P2 | 2/2009 | Shaw et al. |
| PP20,248 | P3 | 9/2009 | Rogers et al. |
| PP20,701 | P2 | 2/2010 | Gilford et al. |
| PP20,731 | P2 | 2/2010 | Mowrey et al. |
| PP20,733 | P2 | 2/2010 | Mowrey et al. |
| PP20,735 | P2 | 2/2010 | Ferguson |
| PP20,775 | P2 | 2/2010 | Mowrey et al. |
| PP20,922 | P2 | 4/2010 | Gilford et al. |
| PP21,538 | P2 | 11/2010 | Gilford et al. |
| PP21,559 | P2 | 12/2010 | Ferguson et al. |
| PP21,762 | P2 | 3/2011 | Stewart et al. |
| PP22,040 | P3 | 7/2011 | Stewart et al. |
| PP22,218 | P2 | 11/2011 | Ferguson |
| PP22,247 | P2 | 11/2011 | Ferguson |
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| 2003/0079263 | P1 | 4/2003 | Gilford et al. |
| 2013/0276182 | P1 | 10/2013 | Fear et al. |

OTHER PUBLICATIONS

Mendoza et al., Unpublished U.S. Appl. No. 15/998,020, filed Jun. 12, 2018, titled "Strawberry Plant Variety Named 'DrisStrawSixtyOne'".

Pakozdi, et al. Unpublished U.S. Appl. No. 15/998,015, filed Jun. 11, 2018, titled "Strawberry Plant Variety Named 'DrisStrawFiftyNine'".

Pakozdi et al., Unpublished U.S. Appl. No. 15/998,028, filed Jun. 14, 2018, titled "Strawberry Plant Variety Named 'DrisStrawSixtyFive'".

Stewart et al., Unpublished U.S. Appl. No. 15/731,415, filed Jun. 6, 2017, titled "Strawberry Plant Variety Named 'DrisStrawFiftyThree'".

Stewart et al., Unpublished U.S. Appl. No. 15/731,421, filed Jun. 6, 2017, titled "Strawberry Plant Variety Named 'DrisStrawFiftySeven'".

Vitten et al., Unpublished U.S. Appl. No. 15/731,559, filed Jun. 27, 2017, titled "Strawberry Plant Variety Named 'DrisStrawFiftyFour'".

Vitten et al., Unpublished U.S. Appl. No. 15/731,560, filed Jun. 27, 2017, titled "Strawberry Plant Variety Named 'DrisStrawFifty Five'".

STRAWBERRY PLANT VARIETY NAMED 'DRISSTRAWSIXTYFOUR'

Latin name: Botanical classification: *Fragaria* x *ananassa*.

Varietal denomination: The varietal denomination of the claimed variety of strawberry plant is 'DrisStrawSixtyFour'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawSixtyFour'.

Strawberry plant variety 'DrisStrawSixtyFour' was discovered in Hillsborough County, Fla. in January of 2012, and originated from a cross between the proprietary female parent 'DrisStrawForty' (U.S. Plant Pat. No. 25,747) and the proprietary male parent 'DrisStrawTwentyThree' (U.S. Plant Pat. No. 23,401). A single plant was selected and asexually propagated via stolons in Shasta County, Calif.

'DrisStrawSixtyFour' was subsequently asexually propagated via stolons, and underwent further testing at a farm in Hillsborough County, Fla. for six years (2011 to 2017). The present variety has been found to be stable and reproduce true to type through successive asexual propagations via stolons.

'DrisStrawSixtyFour' exhibits the following distinguishing characteristics when grown under normal horticultural practices in Hillsborough County, Fla.:

1. Late start of early production; and
2. Fruit having more blunt rather than pointed tips.

'DrisStrawSixtyFour' was selected for the size and shape of its fruit; overall productivity and minimal gaps in production; flavor, texture, and juiciness of its fruit; eating quality throughout season; its plant vigor and health; its plant architecture; and its long and sturdy fruit stems.

DESCRIPTION OF THE DRAWINGS

This new strawberry plant is illustrated by the accompanying photographs which show fruit of the plant, as well as the flowers and leaves. The colors shown are as true as can be reasonably obtained by conventional photographic procedures. The photographs are of plants that are four months old from time of transplant at nursery.

DESCRIPTION OF THE NEW VARIETY

Figure 1:
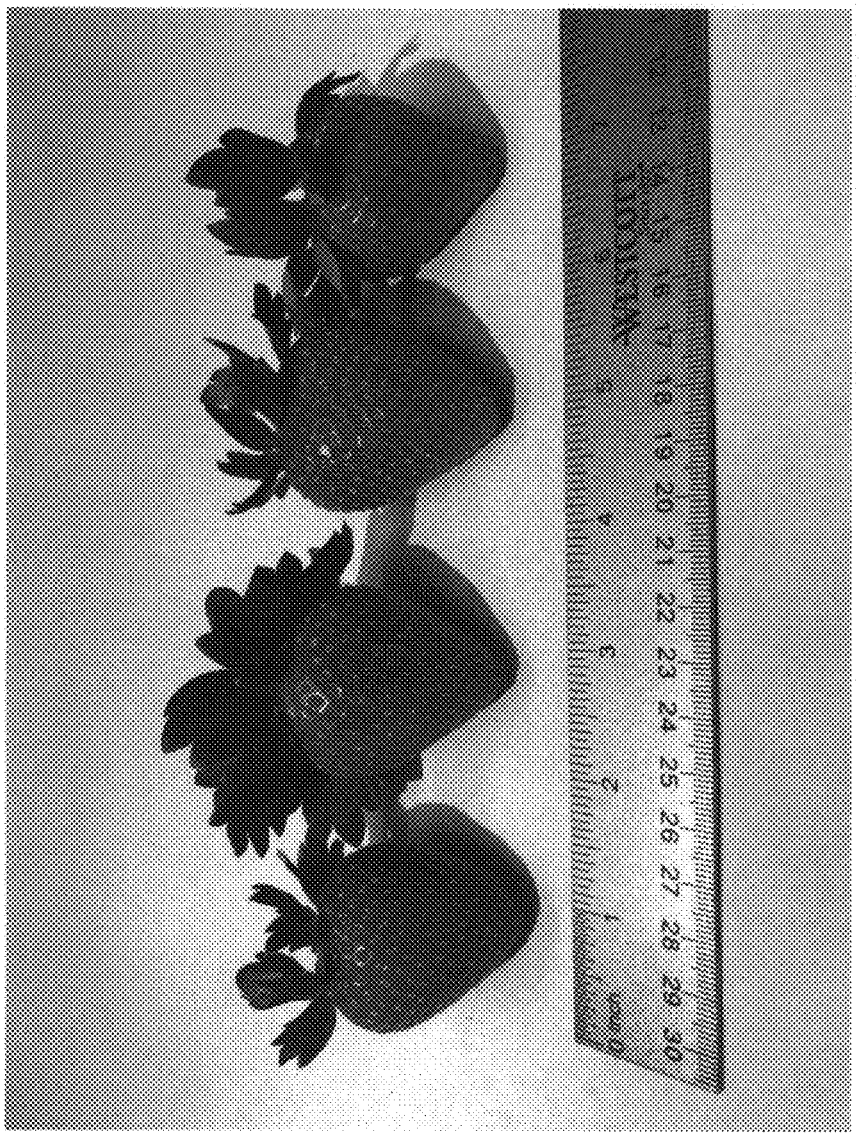
FIG. 1 illustrates whole fruit of variety 'DrisStrawSixtyFour'.
Figure 2:
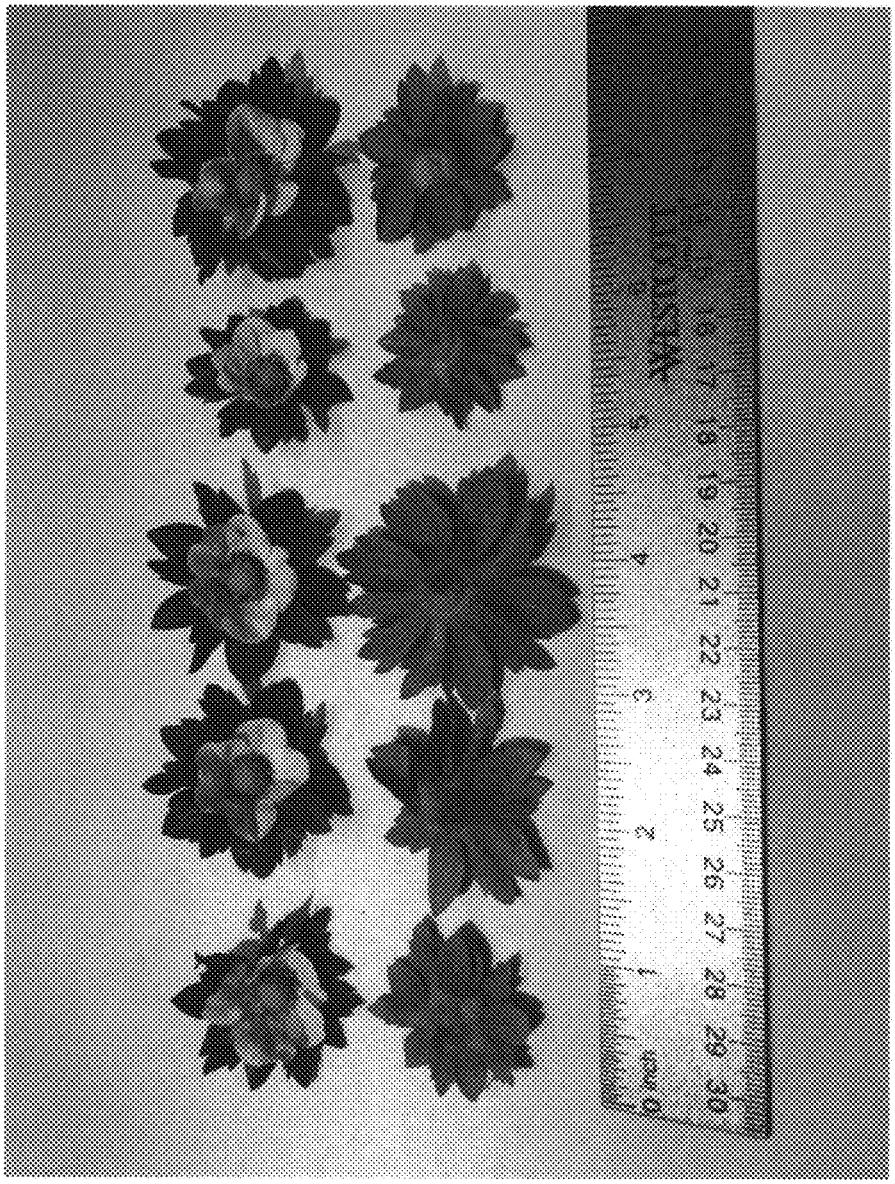
FIG. 2 illustrates the upper and lower surfaces of flowers of variety 'DrisStrawSixtyFour'.
Figures 3A, 3B:
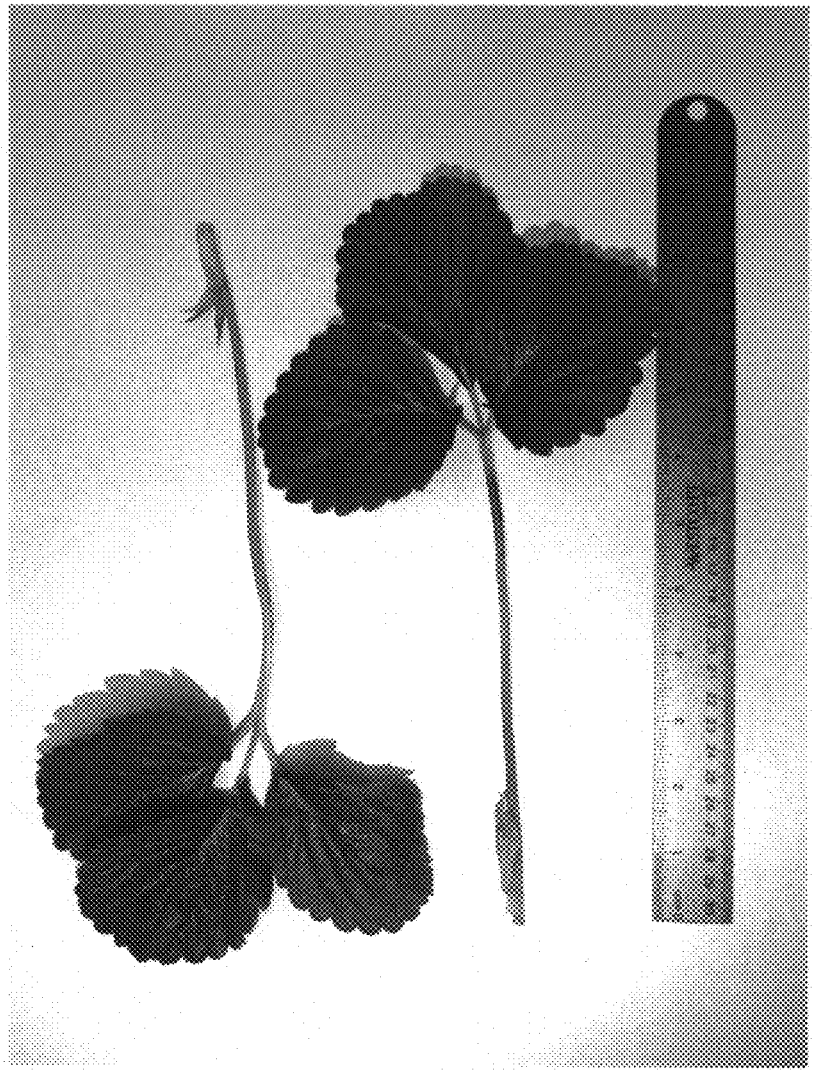
FIG. 3A and FIG. 3B illustrate leaves of variety 'DrisStrawSixtyFour'.
Figure 4:
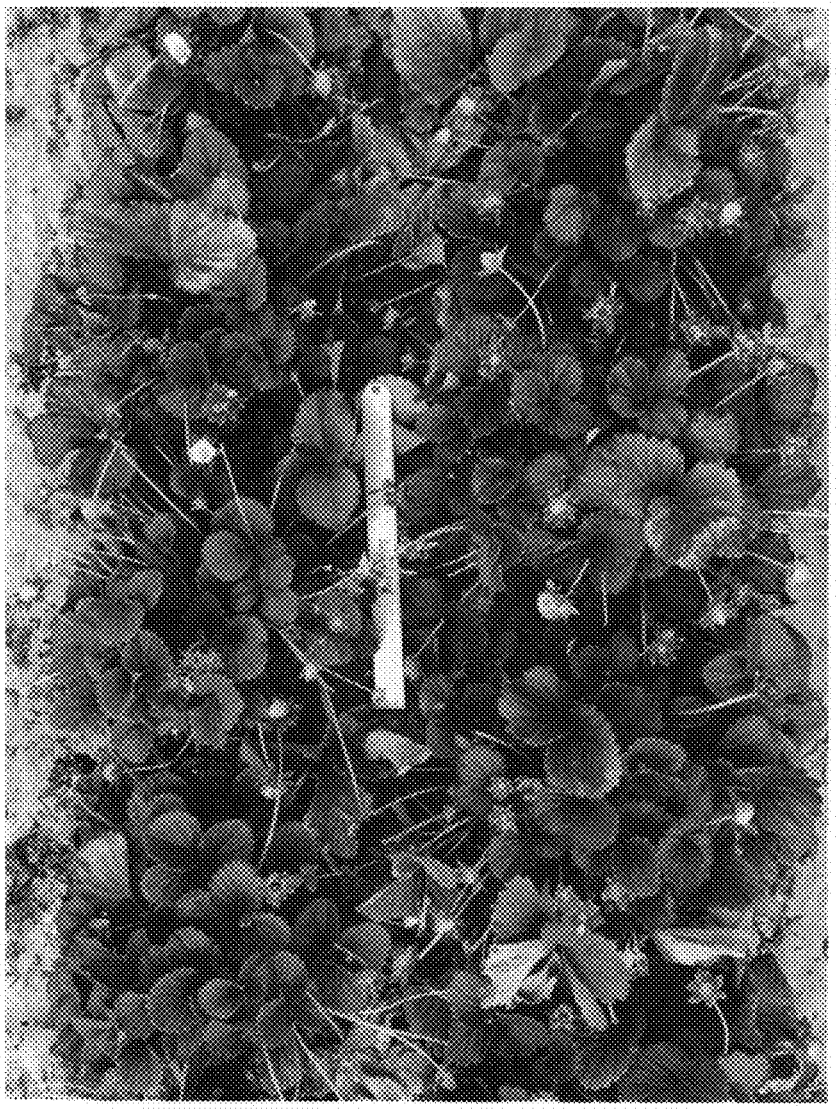
FIG. 4 illustrates the overall plant habit including fruit at various stages of development of variety 'DrisStrawSixtyFour'.

The following detailed descriptions set forth the distinctive characteristics of 'DrisStrawSixtyFour'. The data which define these characteristics is based on observations taken in Hillsborough County, Fla. from 2011 to 2017. This description is in accordance with UPOV terminology. Color designations, color descriptions, and other phenotypical descriptions may deviate from the stated values and descriptions depending upon variation in environmental, seasonal, climatic, and cultural conditions. 'DrisStrawSixtyFour' has not been observed under all possible environmental conditions. The botanical description of 'DrisStrawSixtyFour' was taken from plants that were four months old from time of transplant at nursery. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary, 2$^{nd}$* edition by James G. Harris and Melinda Woolf Harris, unless where otherwise defined.

DETAILED BOTANICAL DESCRIPTION OF THE PLANT

Classification:

*Species.*—*Fragaria* x *ananassa.*

*Common name.*—Strawberry.

*Denomination.*—'DrisStrawSixtyFour'.

Parentage:

*Female parent.*—The proprietary variety 'DrisStrawForty' (U.S. Plant Pat. No. 25,747).

*Male parent.*—The proprietary variety 'DrisStraw TwentyThree' (U.S. Plant Pat. No. 23,401).

Plant:

*Height.*—20.8 cm.

*Diameter.*—36.8 cm.

*Number of crowns per plant.*—4.

*Growth habit.*—Spreading.

Stolon:

*Average number of daughter plants per square foot.*—11.

*Diameter at bract.*—3.68 mm.

*Anthocyanin coloration.*—Present.

*Anthocyanin color.*—RHS 80C (Light purple).

Leaf:

*Number of leaflets.*—Three only.

*Color of upper surface.*—RHS 147A (Moderate olive green).

*Color of lower surface.*—RHS 148A (Yellow-green).

*Variegation.*—Absent.

*Terminal Leaflets.*—Length: 7.6 cm. Width: 7.8 cm. Length/width ratio: 1.0. Number of teeth/terminal leaflet: 22. Leaflet shape: Orbicular. Leaflet apex: Rounded. Shape of base: Rounded. Margin: Crenate. Shape in cross section: Concave.

*Petiole.*—Color of petiole: RHS 144B (Yellow-green). Length: 15.1 cm. Diameter: 4.13 mm. Attitude of hairs: Horizontal. Bract frequency (number present on each petiole): 0.

*Petiolule.*—Color of petiolule: RHS 145A (Yellow-green). Length: 14.40 mm. Diameter: 2.44 mm.

*Stipule.*—Length: 4.6 cm. Width: 10.50 mm. Anthocyanin coloration: Present. Anthocyanin color: RHS 58C (Strong pink).

Inflorescence:

*Position in relation to foliage.*—Above.

*Pedicel.*—Pedicel length: 19.3 cm. Pedicel diameter: 0.18 cm. Color of pedicel: RHS 149C (Brilliant yellowish green). Attitude of hairs: Upwards.

*Flower.*—Flower depth: 9.5 mm. Flower diameter (petal tip to petal tip on non-flattened flower): 24.61 mm. Arrangement of petals: Overlapping. Stamen: Present. Typical and observed number of flowers per plant: 7.9.

*Petal.*—Petal shape: Orbicular. Petal apex: Rounded. Petal margin: Entire (smooth). Petal base: Concave to convex. Length: 10.71 mm. Width: 11.45 mm. Length/width ratio: 0.9. Typical and observed petal number: 5. Color of upper side: RHS 155C (Greenish white). Color of lower side: RHS 155C (Greenish white).

*Calyx.*—Diameter (sepal tip to sepal tip, measured on back of flower): 37.22 mm.

*Sepal.*—Sepal shape: Oblong to oval. Sepal apex: Convex. Sepal margin: Entire (smooth). Color of upper side: RHS 144A (Strong yellowish green). Color of lower side: RHS 144D (Light yellowish green). Length (sepal tip to point of attachment to receptacle): 15.42 mm. Width: 8.62 mm. Typical and observed sepal number: 11.

Fruit:

*Length.*—42.24 mm.

*Width.*—38.86 mm.

*Length/width ratio.*—1.1.

*Weight.*—27.5 grams.

*Fruit hollow length.*—15.31 mm.

*Fruit hollow width.*—3.98 mm.

*Fruit hollow length/width ratio.*—3.8.

*Shape.*—Conical.

*Color.*—RHS 46A (Strong red).

*Position of achenes.*—Level with surface.

*Color of achenes.*—RHS 46A (Strong red).

*Position of calyx attachment.*—Inserted.

*Attitude of sepals.*—Outwards.

*Color of flesh (excluding core).*—RHS 46B (Vivid red).

*Color of core.*—RHS 42B (Strong reddish orange).

Fruiting truss:

*Truss length.*—19.3 cm.

*Truss diameter at base.*—0.18 cm.

*Number of berries per truss.*—1.

*Color of truss.*—RHS 144A (Dark green).

Production:

*Flowering interval.*—Late November to late March.

*Harvest interval.*—Early December to late March.

*Type of bearing.*—Partially remontant.

*Productivity.*—0.439 kg/plant to 0.889 kg/plant of fruit per season from 7-month-old plants when grown in Hillsborough County, Fla.

Resistance to abiotic stress, pests, and diseases:

*Heat.*—Moderately resistant.

*Two-spotted spider mite (Tetranychus urticae).*—Moderately susceptible.

*Broad mite (Polyphagotarsonemus latus).*—Susceptible.

*Botrytis fruit rot (Botrytis cinerea).*—Susceptible.

*Powdery mildew (Podosphaera macularis).*—Moderately susceptible.

*Anthracnose fruit rot (Colletotrichum acutatum).*—Susceptible.

*Anthracnose crown rot (Colletotrichum gloeosporioides).*—Susceptible.

*Charcoal rot (Macrophomina phaseolina).*—Moderately resistant.

*Angular leaf spot (Xanthomonas fragariae).*—Moderately susceptible.

COMPARISON WITH PARENTAL AND COMMERCIAL VARIETIES

'DrisStrawSixtyFour' differs from the proprietary female parent 'DrisStrawForty' (U.S. Plant Pat. No. 25,747) in that 'DrisStrawSixtyFour' produces fruit with more blunt rather than pointed tips compared to fruit of 'DrisStrawForty'.

'DrisStrawSixtyFour' differs from the proprietary male parent 'DrisStrawTwentyThree' (U.S. Plant Pat. No. 23,401) in that 'DrisStrawSixtyFour' produces fruit with more blunt rather than pointed tips compared to fruit of 'DrisStrawTwentyThree'.

'DrisStrawSixtyFour' differs from the commercial variety 'DrisStrawTwentyFour'(U.S. Plant Pat. No. 23,378) in that early production of 'DrisStrawSixtyFour' begins about two weeks behind that of 'DrisStrawTwentyFour'. Further, plants of 'DrisStrawSixtyFour' have inflorescence above foliage, while plants of 'DrisStrawTwentyFour' have inflorescence beneath foliage. Additionally, fruit of 'DrisStrawSixtyFour' have absent or a very narrow width of band without achenes, while fruit of 'DrisStrawTwentyFour' have a broad width of band without achenes. Moreover, fruit of 'DrisStrawSixtyFour' have a calyx attachment that is inserted in fruit, while fruit of 'DrisStrawTwentyFour' have a calyx attachment that is raised from fruit.

'DrisStrawSixtyFour' differs from the commercial variety 'DrisStrawFortyNine' (U.S. Plant Pat. No. 27,682) in that early production of 'DrisStrawSixtyFour' begins just after that of 'DrisStrawFortyNine'. Further, plants of 'DrisStrawSixtyFour' have a spreading growth habit, while plants of 'DrisStrawFortyNine' have a semi-upright to spreading growth habit. Additionally, plants of 'DrisStrawSixtyFour' have strong vigor, while plants of 'DrisStrawFortyNine' have weak to medium vigor. Moreover, fruit of 'DrisStrawSixtyFour' have absent or a very narrow width of band without achenes, while fruit of 'DrisStrawFortyNine' have a broad width of band without achenes.

We claim:

1. A new and distinct variety of strawberry plant named 'DrisStrawSixtyFour' as shown and described herein.

* * * * *